(12) United States Patent
Scaliante et al.

(10) Patent No.: US 6,662,653 B1
(45) Date of Patent: Dec. 16, 2003

(54) SENSOR ASSEMBLIES AND METHODS OF SECURING ELONGATED MEMBERS WITHIN SUCH ASSEMBLIES

(75) Inventors: Ademir Scaliante, Sertãozinho (BR); Geraldo Gullo, Sertãozinho (BR)

(73) Assignee: Smar Research Corporation, Holbrook, NY (US)

( * ) Notice: Subject to any disclaimer, the term of this patent is extended or adjusted under 35 U.S.C. 154(b) by 0 days.

(21) Appl. No.: 10/253,741

(22) Filed: Sep. 23, 2002

(51) Int. Cl.[7] .................................................. G01N 9/00
(52) U.S. Cl. ........................................... 73/448; 73/449
(58) Field of Search ..................... 73/437, 439, 32 R, 73/32 A, 434, 448, 449, 61.46, 53.01; 702/137, 138

(56) References Cited

U.S. PATENT DOCUMENTS

| | | |
|---|---|---|
| 5,604,315 A | 2/1997 | Briefer et al. |
| 5,811,690 A | 9/1998 | Hershey |
| 5,827,963 A | 10/1998 | Selegatto et al. |
| 5,899,962 A | 5/1999 | Louwagie et al. |
| 6,234,019 B1 | 5/2001 | Caldeira |

*Primary Examiner*—Helen Kwok
(74) *Attorney, Agent, or Firm*—Baker Botts LLP

(57) ABSTRACT

An assembly and a method of securing elongated members within the assembly are provided. In particular, one or more particular elongated members which are adapted to contain a particular fluid may be affixed to a temperature-conducting (e.g., metallic) arrangement, and a portion of the assembly may be positioned within a container containing a sample fluid. For example, the temperature-conducting arrangement can be configured to provide the particular elongated member therethrough, and the particular fluid can be a sensor fluid. Further, the temperature-conducting arrangement is affixed to a further elongated member which is configured to provide the temperature-conducting arrangement therethrough. Moreover, the metallic arrangement may maintain a temperature of the particular fluid is provided so that it is substantially the same as a temperature of the sample fluid.

36 Claims, 7 Drawing Sheets

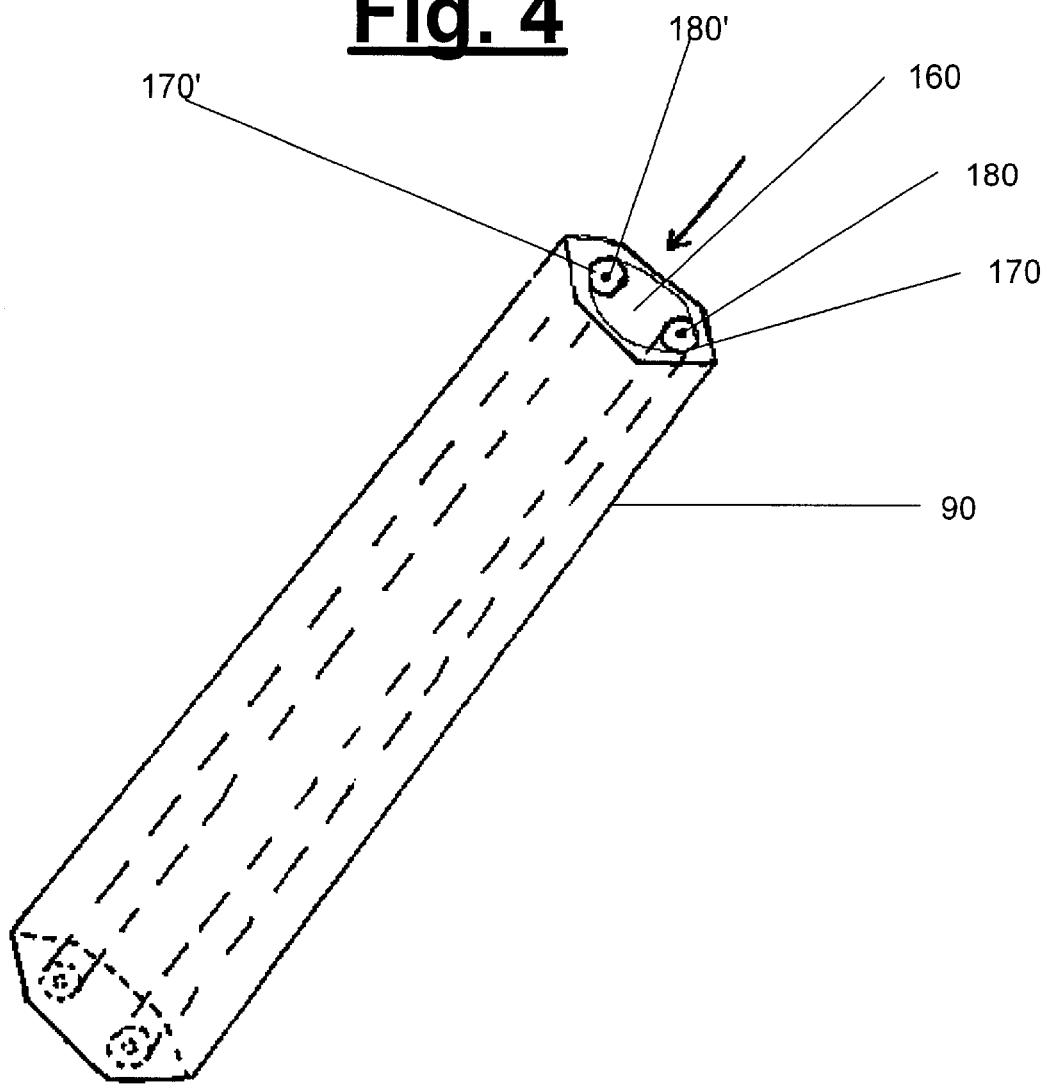

SENSOR ASSEMBLIES AND METHODS OF SECURING ELONGATED MEMBERS WITHIN SUCH ASSEMBLIES

FIELD OF THE INVENTION

The present invention relates generally to an assembly, such as a sensor assembly positioned within a container containing a sample fluid, and methods of securing elongated members within such assembly. Specifically, the present invention is directed to an assembly and method in which a metallic arrangement is configured to provide therethrough one or more elongated members containing a particular fluid, and is adapted to maintain a temperature of the particular fluid to be substantially the same as a temperature of the sample fluid.

BACKGROUND OF THE INVENTION

Conventional assemblies (e.g., conventional sensor assemblies) may be used to determine a characteristic of a sample fluid within a container (e.g., within a tank). For example, as described in U.S. Pat. No. 6,234,019, the entire disclosure of which is incorporated herein by reference, the conventional assemblies can be used to determine a temperature of the sample fluid, a pressure associated with the sample fluid, a density of the sample fluid, etc. An exemplary conventional assembly may be affixed to a tank, and can include a housing assembly positioned within the tank. The conventional assembly also may include a first sensor positioned within the tank at a first fluid level of the sample fluid, in which the first sensor is adapted to detect a fluid pressure at the first fluid level. Conventional assembly can also include a second sensor positioned within the tank at a second fluid level below the first fluid level, in which the second sensor is adapted to detect a fluid pressure at the second fluid level. Moreover, a transmitter can also be provided which is adapted to communicate with the first sensor and with the second sensor, and a determining device that is coupled to the transmitter. The transmitter can be further adapted to generate signals corresponding to the density of the sample fluid, and the determining device may be adapted to determine the density of the sample fluid based on such signals.

The first sensor of the conventional assemblies may be in communication with the transmitter via a first tube situated within an opening which is formed through a first rod. The first rod can be positioned within the housing arrangement between the first sensor and the transmitter. Moreover, the first tube can contain a first sensor fluid, and when the first sensor senses the fluid pressure at the first fluid level, the first sensor acts on the first sensor fluid. For example, the first sensor can displace the first sensor fluid, and an amount of the displacement of the first sensor fluid depends on the fluid pressure at the first fluid level. The transmitter can subsequently communicate with the first sensor via the first sensor fluid.

Similarly, the second sensor may be in communication with the transmitter via a second tube situated within an opening which is formed through a second rod. The second rod can be positioned within the housing arrangement between the second sensor and the transmitter, or alternatively, may be positioned within the housing arrangement between the second sensor and the first sensor. Moreover, if the second rod is positioned between the second sensor and the first sensor, the second tube can be provided inside the second rod and the first rod. The second tube can contain a second sensor fluid, and when the second sensor senses the fluid pressure at the second fluid level, the second sensor acts on the second sensor fluid. For example, the second sensor can displace the second sensor fluid, and an amount of the displacement of the second sensor fluid depends on the fluid pressure at the second fluid level. The transmitter can subsequently communicate with the second sensor via the second sensor fluid. Moreover, based on the displacement of the first sensor fluid and the second sensor fluid, the transmitter can generate the signals corresponding to the density of the sample fluid, and the determining device can determine the density of the sample fluid based on such signals.

Nevertheless, in the conventional sensor assembly, when the opening is provided through the first rod and/or the second rod, (e.g., by drilling), it may be difficult to form an opening having a diameter which is substantially the same as a diameter of the first tube and/or the second tube, respectively. Specifically, the diameter of the opening may be substantially greater than the diameter of the first tube and/or the second tube. As such, after the first tube and/or the second tube is inserted inside the first rod and/or the second rod, respectively, there may be air gaps, e.g., voids, provided within the first rod and/or the second rod. When the conventional sensor assembly is positioned inside the tank, such air gaps may adversely affect a transfer of energy between the sample fluid and the first sensor fluid and/or the second sensor fluid.

Consequently, a temperature of the sample fluid may be different than a temperature of the first sensor fluid and/or a temperature of the second sensor fluid. Similarly, the temperature of the first sensor fluid may be different than the temperature of the second sensor fluid. When the temperature of the sample fluid is different than the temperature of the first sensor fluid and/or the temperature of the second sensor fluid, the fluid pressure detected at the first fluid level and/or the second fluid level may be inaccurate. Similarly, when the temperature of the first sensor fluid is different than the temperature of the second sensor fluid, the detected fluid pressure may be inaccurate due to thermal expansion. Consequently, due to this inconsistency, the density of the sample fluid determined by the determining device may also be inaccurate.

SUMMARY OF THE INVENTION

Therefore, a need has arisen to provide an assembly, such as a sensor assembly, and a method of securing elongated members within such assembly, which overcome the above-described and other shortcomings of the prior art.

One of the advantages of the present invention is that the assembly, and method are adapted to maintain a temperature of the particular fluid substantially the same as a temperature of the sample fluid. For example, the construction of the assembly of the present invention may prevent air gaps from being provided within an elongated member thereof.

This and other advantages can be achieved with an exemplary embodiment of the assembly and method according to the present invention. This assembly, such as a sensor assembly positioned within a container containing a sample fluid, and the method of securing elongated members within the assembly, are provided for at least such purpose. In particular, one or more of the elongated members (e.g., one or more first tubes, such as metallic tubes) which are adapted to contain a particular fluid may be affixed (e.g., soldered or welded) to a temperature-conducting (e.g., metallic) arrangement. For example, the metallic arrangement can be configured to provide the elongated member therethrough, and the elongated member can have an opening adapted to contain the particular fluid.

In one preferred exemplary embodiment of the present invention, the opening can be a groove formed through (by drilling, chiseling, etc.) an outer surface (e.g., a side portion) of the metallic arrangement, and the particular elongated member can be inserted into the groove via the side portion of the metallic arrangement. In this exemplary embodiment, the arrangement can be soldered to the metallic arrangement such that the solder forms a portion of the outer surface of the metallic arrangement. Further, the metallic arrangement can be affixed (e.g., soldered or welded) to a further elongated member (e.g., a second tube) which is configured to provide the metallic arrangement therethrough. Moreover, the metallic arrangement may maintain a temperature of the particular fluid to be substantially the same as a temperature of the sample fluid. For example, the elongated member can be provided through an opening in the metallic arrangement, and can be affixed to the metallic arrangement using solder. After the elongated member is affixed to the metallic arrangement, the metallic arrangement can be provided through an opening in the further elongated member. Moreover, the metallic arrangement can be affixed to the further elongated member using solder.

According to another exemplary embodiment of the present invention, the assembly can be a sensor assembly. The sensor assembly can include a sensor housing arrangement. In this exemplary embodiment, the further elongated member may be positioned inside the housing arrangement. The sensor assembly also can include a first sensor which is coupled to the housing arrangement or positioned inside the housing arrangement, and the first sensor may be adapted to detect a first fluid pressure of the sample fluid at a first fluid level by acting on the particular fluid. Moreover, the elongated member can include a pair of particular elongated members. For example, a first one of the pair of the elongated members can be adapted to contain the particular fluid, and a second one of this pair can be adapted to contain a further fluid. In this embodiment of the present invention, the metallic arrangement may be further adapted to maintain the temperature of the particular fluid to be substantially the same as a temperature of the further fluid, thereby reducing or even eliminating the problems associated with thermal expansion.

In another exemplary embodiment of the present invention, the sensor assembly can also include a second sensor which is coupled to the housing arrangement or positioned inside the housing arrangement, and the second sensor may adapted to detect a second fluid pressure of the sample fluid at a second fluid level by acting on the further fluid. Moreover, the sensor assembly can include a transmitter situated externally from the container, which is coupled to the housing arrangement or positioned inside the housing arrangement. The transmitter may be adapted to communicate with the first sensor via the particular fluid, and with the second sensor via the further fluid. The transmitter also can be adapted to generate signals corresponding to a density of the sample fluid. The sensor assembly can include a determining device coupled to the transmitter, and the determining device may be adapted to determine the density of the sample fluid based on the signals.

In any of the foregoing exemplary embodiment and other embodiments or variations of the present invention, the metallic arrangement can also be adapted to maintain a first temperature of the particular fluid and/or the further fluid provided at a first end of one of the particular elongated members to be substantially the same as a second temperature of the particular fluid and/or the further fluid provided at a second end of the particular elongated member.

BRIEF DESCRIPTION OF THE DRAWINGS

FIG. 4 is a schematic diagram of an exemplary embodiment of the metallic arrangement of FIG. 3 affixed to a further elongated member according to the present invention.

DETAILED DESCRIPTION

Exemplary embodiments of the present invention and their advantages may be understood by referring to FIGS. 1–5, like numerals being used for like corresponding parts in the various drawings.

Figure 1:
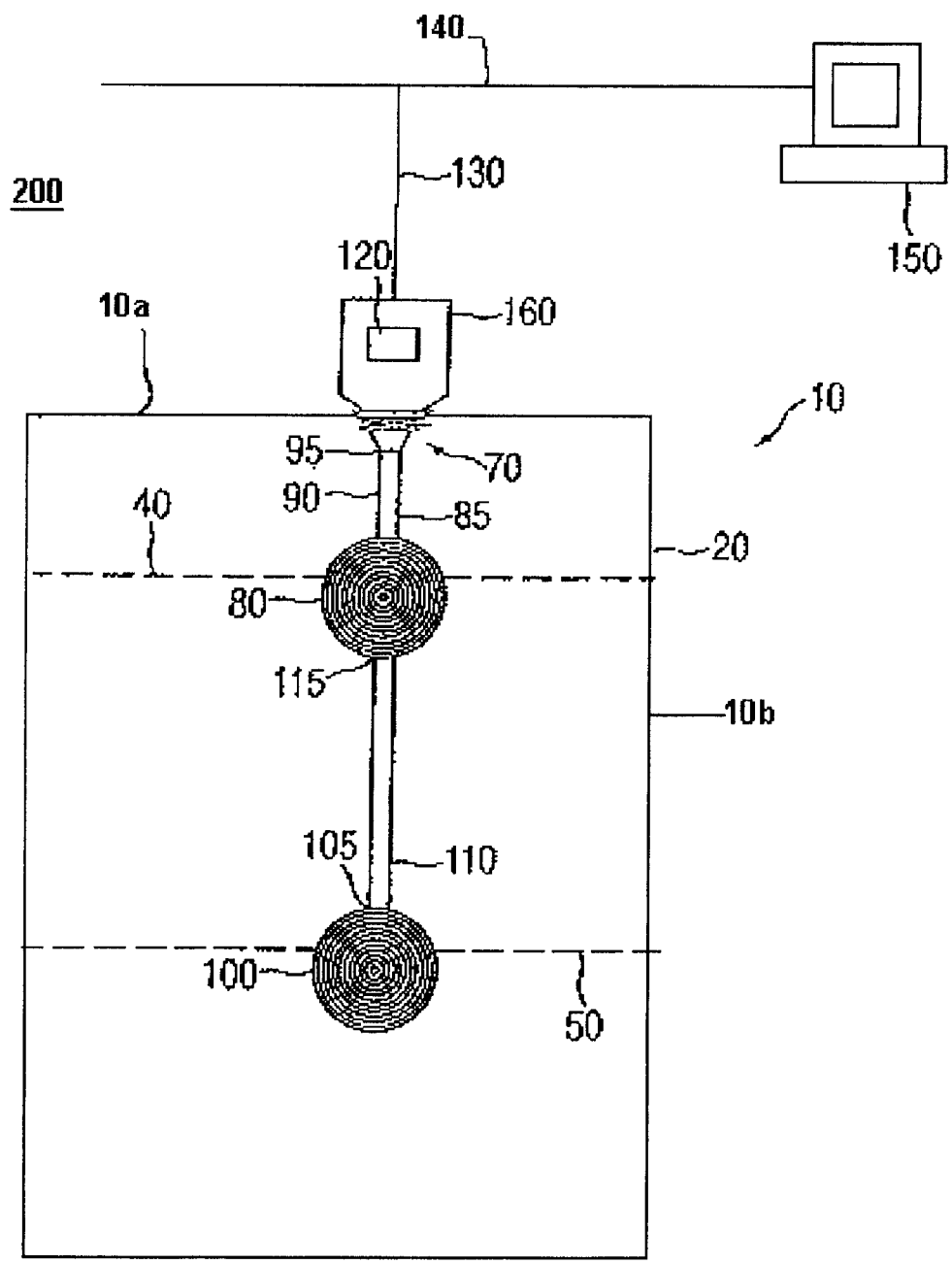
FIG. 1 is a schematic diagram of a first exemplary embodiment of an assembly according to the present invention for determining a characteristic of a fluid within a container.

Referring to FIG. 1, an exemplary embodiment of an assembly 200 (e.g., a sensor assembly) for determining a characteristic of a sample fluid 20 (e.g., beer) within a container a tank, such as a beer tank) is provided. For example, the particular arrangement illustrated in FIG. 1 may be similar to an arrangement described in U.S. Pat. No. 6,234,019. Specifically, the assembly 200 may include a housing arrangement 70, a first sensor 80, a first elongated member 90 (e.g., a tube), a second sensor 100, a second elongated member 110 (e.g., a tube), a transmitter 120, a first data bus 130, a second data bus 140, and a computer system 150.

Figure 2:
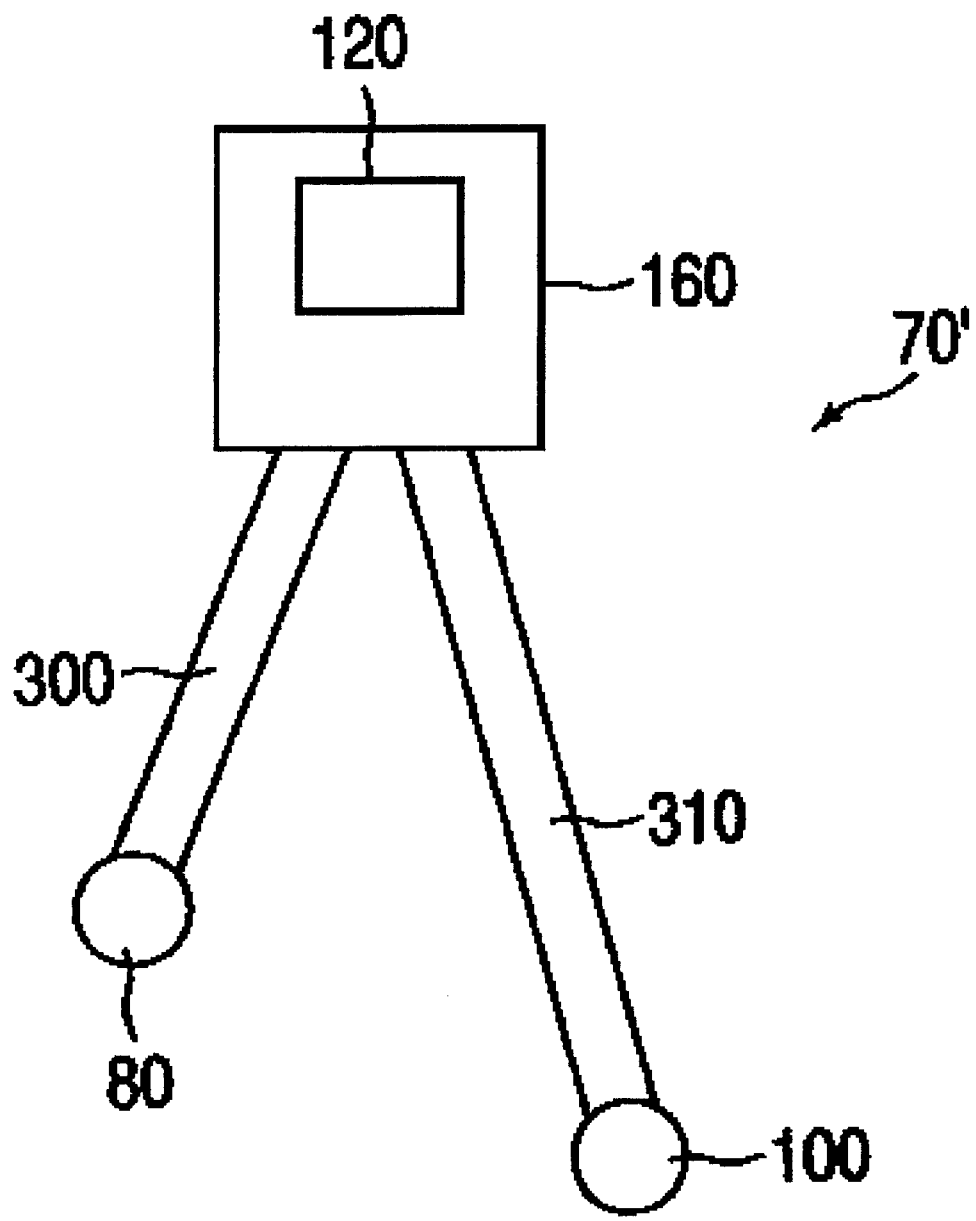
FIG. 2 is a schematic diagram of a second exemplary embodiment of the assembly according to the present invention for determining the characteristic of the fluid within the container.

The housing arrangement 70 can include the first elongated member 90 and/or the second elongated member 110. The first sensor 80, the second sensor 100, and/or the transmitter 120 can be provided within the housing arrangement 70. Alternatively, the first sensor 80, the second sensor 100 and/or the transmitter 120 can be provided within the housing arrangement 70, or may be externally coupled to the housing arrangement 70. For example, the transmitter 120 can be positioned outside from a container 10, and first sensor 80 and second sensor 100 can be positioned inside the container 10. The first elongated member 90 may have a first end 85 and a second end 95. Similarly, the second elongated member 110 can have a first end 105 and a second end 115. Moreover, the first end 105 of the second elongated member 110 can be coupled to the second sensor 100, and the second end 115 of the second elongated member 110 may be coupled to the first sensor 80. Further, the first end 85 of the first elongated member 90 can be coupled to the first sensor 80, and the second end 95 of the first elongated member 90 may be coupled to a container portion 160 of the housing arrangement 70. The transmitter 120 may be coupled to the container portion 160, or alternatively, can be positioned inside the container portion 160. For example, the first elongated member 90 can be vertically aligned with the second elongated member 110, such that the first elongated member 90 and the second elongated tube 110, 100 are provided as a single tube separated by the first sensor 80. As depicted in FIG. 2, in an alternative embodiment of the present invention, a first elongated member 300 and a second elongated member 310 can be separate members (e.g., tubes) extending from the container portion 160.

In another exemplary embodiment of the present invention, the transmitter 120 can be coupled to the first data bus 130 (e.g., a high speed bus, such as a Fieldbus, etc.), and the first data bus can be coupled to a second data bus 140 (e.g., a high speed bus, such as a Fieldbus, etc.) as shown in FIG. 1. Moreover, the second data bus 140 can be coupled to the computer system 150, such that the transmitter 120 may be in communication with the computer system 150 via the first data bus 130 and the second data bus 140. In this exemplary embodiment of the present invention, there may be a plurality of first data buses 130 coupled to the computer system 150 via the second data bus 140, such that a plurality of transmitters 120 associated with different containers 10 may be in communication with the computer system 150. Alternatively, the second data bus 140 can be eliminated from the assembly 200, and the first data bus 130 can be directly coupled to the computer system 150.

In operation, and as discussed in more detail with respect to FIGS. 3, 3a, 4, and 4a, the container 10 may contain the sample fluid 20, and a sensor fluid (e.g., a static sensor fluid, such as silicon oil, fluorolube oil, silicone oil, propylene glycol oil, etc.) can be provided within an opening 180 of a third elongated member 170 (shown in FIGS. 3 and 4) and/or an opening 180' of a fourth elongated member 170' (shown in FIGS. 3 and 4) which are situated within the housing arrangement 70. As such, the housing arrangement 70 maintains the sensor fluid separate from the sample fluid 20. As described in detailed in U.S. Pat. No. 6,234,019, the first sensor 80 and/or the second sensor 100 can communicate with the transmitter 120 via the sensor fluid. For example, a first portion of the sensor fluid can be provided within the third elongated member 170, and a second portion of the sensor fluid can be provided within the fourth elongated member 170'. Moreover, the first sensor 80 may act on (e.g., displace) the first portion of the sensor fluid, and the second sensor 100 may act on (e.g., displace) the second portion of the sensor fluid.

Specifically, a portion of the housing arrangement 70 may be lowered into the sample fluid 20, such that the first sensor 80 is situated within the sample fluid 20 at a first fluid level 40, and the second sensor 100 is situated within the sample fluid 20 at a second fluid level 50. The assembly 200 then can be affixed to the container 10 (e.g., via a side wall 10b or a top portion 10a of the container 10). After the assembly 200 is affixed to the container 10, the first sensor 80 may sense the fluid pressure at the first fluid level 40, and the second sensor 100 may sense the fluid pressure at the second fluid level 50. Moreover, the pressure sensed by the first sensor 80, e.g., due to a deflection of its diagram may displace the first portion of the sensor fluid. Similarly, the pressure sensed by the second sensor 100, e.g., also due to a deflection of its diagram, may displace the second portion of the sensor fluid. Further, the transmitter 120 can transmit one or more signals including data associated with the displacement of the sensor fluid, and the computer system 150 can calculate a density of the sample fluid based on such data.

Figure 3:
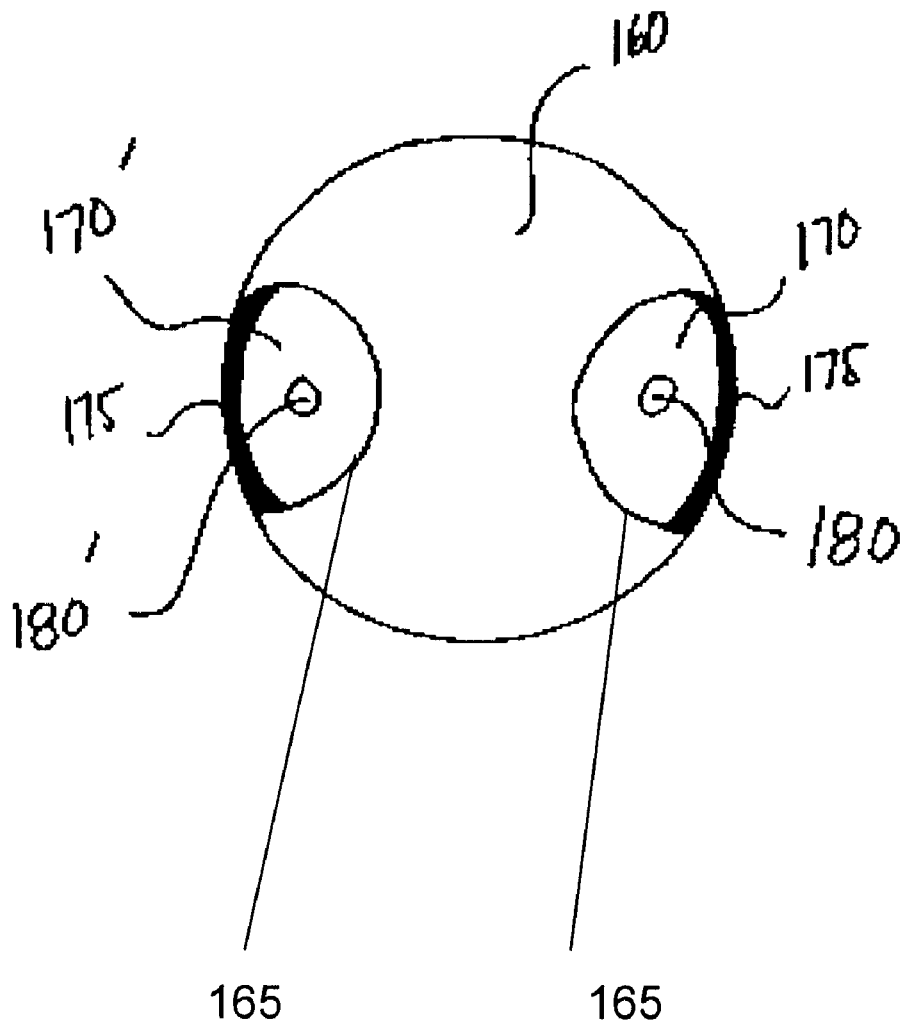
FIG. 3 is a schematic diagram of an exemplary embodiment of an elongated member affixed to a metallic arrangement according to the present invention.
Figure 3A:
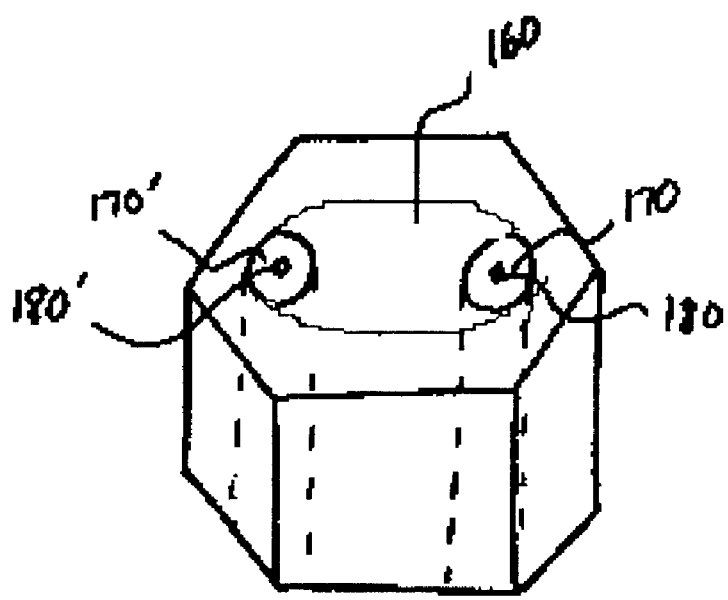
FIG. 3a is a partial schematic diagram of an exemplary embodiment of the metallic arrangement of FIG. 3 affixed to a further elongated member according to the present invention.

Referring to FIGS. 3 and 3a, as described above, the sensor fluid can be provided within the third elongated member 170 and/or the fourth elongated member 170' which are situated within the housing arrangement 70. Specifically, the assembly 200 also may include a metallic arrangement 160, and one or more openings 165 (e.g., holes, grooves, etc.) may be provided through the metallic arrangement 160. The diameter of the openings 165 may be substantially the same as a diameter of the third elongated member 170 and/or the fourth elongated member 170', respectively. For example, the diameter of the openings 165 can be slightly greater than the diameter of the third elongated member 170 and/or the fourth elongated member 170', respectively, such that the third elongated member 170 and/or the fourth elongated member 170' may be situated within the openings 165.

In one preferred embodiment of the present invention, holes or fares (not shown) can be formed through the metallic arrangement 160 by drilling, chiseling, etc. In another preferred embodiment of the present invention, each of the openings 165 can be a groove 165 formed through (e.g., by drilling, chiseling, etc.) an outer surface (i.e., a side portion) of the metallic arrangement 160, and the third elongated member 170 and/or the fourth elongated member 170' can be inserted into one of the grooves 165 of the metallic arrangement 160 via the side portion of the metallic arrangement 160. In this exemplary embodiment, the third elongated member 170 and/or the fourth elongated member 170' can be soldered to the metallic arrangement 160 such that the solder 175 forms a portion of the outer surface of the metallic arrangement 160. Moreover, the metallic arrangement 160 can extend for a length which is substantially the same as a length of the first elongated member 90 and/or a length of the second elongated member 110.

In another exemplary embodiment of the present invention, the third elongated member 170 and/or the fourth elongated member 170' can be made of a metallic material, such that the third elongated member 170 and/or the fourth elongated member 170' can be affixed (e.g., soldered using solder 175 or welded) to the metallic arrangement 160. Consequently, there may be an elimination or a substantially reduction of air gaps or voids provided between the metallic arrangement 160 and the third elongated member 170 and/or the fourth elongated member 170'. Moreover, the third elongated member 170 and/or the fourth elongated member 170' may include openings 180, 180', respectively, which may be adapted to contain the sensor fluid.

Figure 4A:
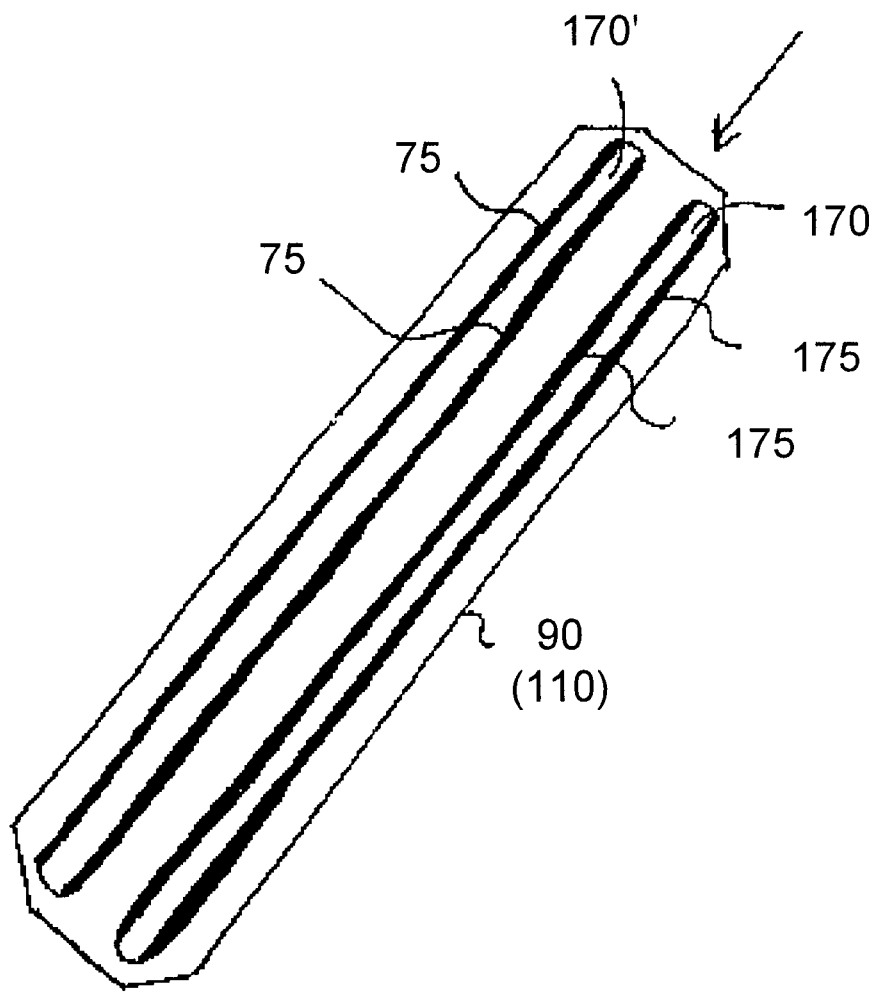
FIG. 4a is an cross-sectional view of an exemplary embodiment of the particular elongated member affixed to the metallic arrangement of FIG. 3 using solder.

Referring to FIGS. 4 and 4a, in an exemplary embodiment of the present invention, after the third elongated member 170 and/or the fourth elongated member 170' are affixed to the metallic arrangement 160, the metallic arrangement 160 can be affixed (e.g., soldered using solder 175 or welded) to the first elongated member 90 and/or the second elongated member 110. Consequently, there may not be air gaps or voids provided between the metallic arrangement 160 and the first elongated member 90 and/or the second elongated member 110. Alternatively, the metallic arrangement 160 can be affixed to the first elongated member 300 and/or the second elongated member 310. Nevertheless, it will readily be understood by those of ordinary skill in the art that the number of metallic arrangements 160 employed in the assembly 200 may correspond either or indirectly, to the number of sensors employed in the assembly 200. For example, when the assembly 200 employs two sensors, the assembly 200 may also employ two metallic arrangements 160. Moreover, the first elongated member 90 and/or the second elongated member 110 can be provided within the housing arrangement 70, and the assembly 200 can be positioned inside the container 10 in order to determine the characteristics of the sample fluid 20 as set forth above.

In any of the forgoing exemplary embodiments of the present invention described herein, because the metallic arrangement 160 may reduce or even eliminate air gaps or void from being provided within the first elongated member 90 and/or the second elongated member 110, the metallic arrangement 160 may be adapted to maintain a temperature of the sensor fluid to be substantially the same as the temperature of the sample fluid 20. Specifically, due to such implementation, the transfer of energy between the sample fluid 20 and the sensor fluid may not likely be adversely affected by such air gaps or voids. Similarly, the metallic arrangement 160 also may be adapted to maintain the temperature of the first portion of the sensor fluid which is contained in opening 180 to be substantially the same as the temperature of the second portion of the sensor fluid which is contained in opening 180', thereby reducing the problems associated with a thermal expansion. Moreover, the metallic arrangement 160 can be adapted to maintain the temperature of the sensor fluid provided at the first end 85 of the first elongated member 90 to be substantially the same as the temperature of the sensor fluid provided at a second end 95 of the first elongated member 90. Similarly, the metallic arrangement 160 can be adapted to maintain the temperature of the sensor fluid provided at the first end 105 of the second elongated member 110 to be substantially the same as the temperature of the sensor fluid provided at a second end 115 of the second elongated member 110.

Figure 5:
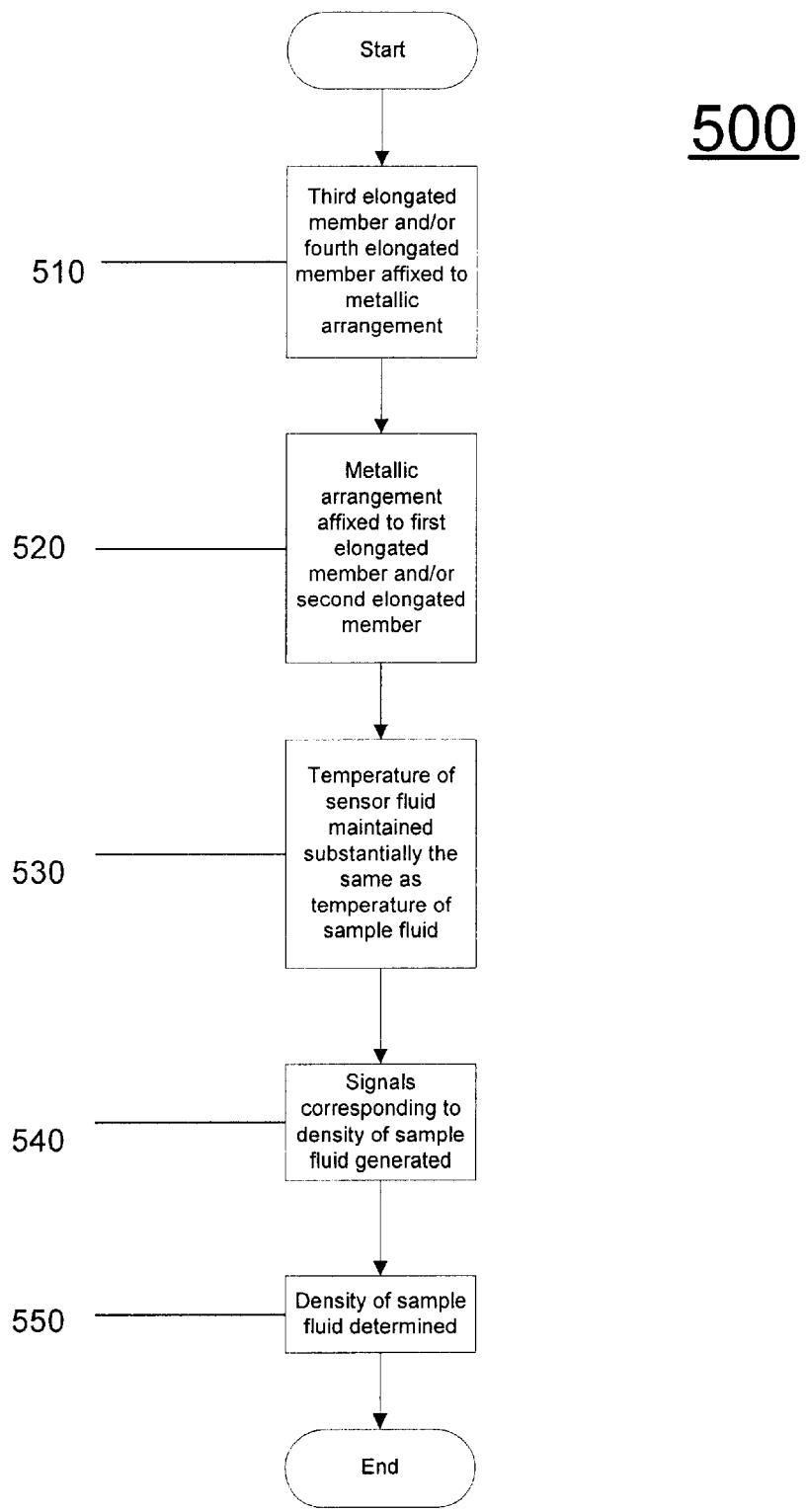
FIG. 5 is a flow diagram of an exemplary embodiment of a method according to the present invention for securing tubes within the assembly.

Referring to FIG. 5, an exemplary embodiment of a method 500 according to the present invention for securing elongated members with the assembly 200 is depicted. In step 510, the third elongated member 170 and/or the fourth elongated member 170' can be affixed (e.g., soldered using solder 175 or welded) to the metallic arrangement 160. In step 520, the metallic arrangement 160 can be affixed (e.g., again soldered using solder 175 or welded) to the first elongated member 90 and/or the second elongated member 110. After steps 510 and 520, the assembly can be positioned inside the container 10 containing the sample fluid, such that in step 530, the temperature of the sensor fluid may be maintained substantially the same as the temperature of the sample fluid. Similarly, in step 530, the temperature of the first portion of the sensor fluid which is contained in the opening 180 can be maintained substantially the same as the temperature of the second portion of the sensor fluid which is contained in the opening 180'. Moreover, in step 540, signals corresponding to the density of the sample fluid are generated, and in step 550, the density of the sample fluid is determined.

While the invention has been described in connecting with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. It is intended that the specification and the described examples are considered as exemplary only, with the true scope and spirit of the invention indicated by the following claims.

What is claimed is:

1. An assembly which has at least one portion positioned within a container containing a sample fluid, comprising:
   at least one particular elongated member adapted to contain a particular fluid therein;
   a temperature-conducting arrangement configured to facilitate at least one portion of the at least one particular elongated member therethrough; and
   at least one further elongated member configured to provide at least one portion of the temperature-conducting arrangement therethrough, wherein the temperature-conducting arrangement is adapted to maintain a temperature of the particular fluid substantially the same as a temperature of the sample fluid.

2. The assembly of claim 1, further comprising a sensor adapted to measure at least one characteristic of the sample fluid wherein the particular fluid is a sensor fluid which is in communication with the sensor.

3. The assembly of claim 2, wherein the sensor fluid is oil.

4. The assembly of claim 3, wherein the oil is at least one of a silicone oil, a fluorolube oil, and a propylene glycol oil.

5. The assembly of claim 1, wherein the at least one particular elongated member is composed of a metallic material.

6. The assembly of claim 1, wherein the temperature-conducting arrangement is composed of a metallic material, and wherein the temperature-conducting arrangement extends for a length which is substantially the same as a length of the at least one further elongated member.

7. The assembly of claim 1, wherein the temperature-conducting arrangement is composed of a metal material, and wherein the temperature-conducting arrangement is configured to provide the at least one particular elongated member therethrough via a groove formed in a side portion of the temperature-conducting arrangement, wherein the at least one particular elongated member is soldered to the temperature-conducting arrangement such that at least one portion of a solder forms at least one portion of the side portion of the temperature-conducting arrangement, and wherein the temperature-conducting arrangement is soldered to the at least one further elongated member.

8. The assembly of claim 1, further comprising a member adapted to be affixed to the container.

9. The assembly of claim 1, further comprising a sensor housing arrangement, wherein the at least one particular elongated member is positioned inside the temperature-conducting arrangement, wherein the temperature-conducting arrangement is positioned inside the at least one further elongated member, and wherein the at least one further elongated member is positioned inside the sensor housing arrangement.

10. The assembly of claim 9, further comprising a first sensor which is one of coupled to the housing arrangement and positioned inside the housing arrangement, wherein the first sensor is adapted to detect a first fluid pressure of the sample fluid at a first fluid level by acting on the particular fluid.

11. The assembly of claim 10, wherein the at least one particular elongated member comprises a pair of particular elongated members, wherein a first one of the pair of particular elongated members is adapted to contain the particular fluid, wherein a second one of the pair of particular elongated members is adapted to contain a further fluid, and wherein the temperature-conducting arrangement is further adapted to maintain the temperature of the particular fluid to be substantially the same as a temperature of the further fluid.

12. The assembly of claim 11, further comprising a second sensor which is one of coupled to the housing arrangement and positioned inside the housing arrangement, wherein the second sensor is adapted to detect a second fluid pressure of the sample fluid at a second fluid level by acting on the further fluid.

13. The assembly of claim 12, further comprising a transmitter situated externally from the container, wherein the transmitter is one of coupled to the housing arrangement and positioned inside the housing arrangement, and wherein the transmitter is adapted to communicate with the first sensor via the particular fluid, and with the second sensor via the further fluid.

14. The assembly of claim 13, wherein the transmitter is further adapted to generate at least one signal corresponding to a density of the sample fluid, wherein at least one of the first sensor and the second sensor is connected to a first end of the at least one further elongated member, and wherein the transmitter is connected to the second end of the at least one further elongated member.

15. The assembly of claim 14, further comprising a determining device coupled to the transmitter, wherein the determining device is adapted to determine the density of the sample fluid based on the at least one signal.

16. The assembly of claim 8, wherein the container is a tank.

17. The assembly of claim 1, wherein the at least one particular elongated member is a tube, and wherein the at least further elongated member is a tube.

18. The assembly of claim 1, wherein the temperature-conducting arrangement is further adapted to maintain a first temperature of the particular fluid provided at a first end of the at least one particular elongated member to be substantially the same as a second temperature of the particular fluid provided at a second end of the at least one particular elongated member.

19. A method of securing elongated members within an assembly, comprising the steps of:
affixing at least one portion of at least one particular elongated member within a temperature-conducting arrangement, the at least one particular elongated member being adapted to contain a particular fluid, the temperature-conducting arrangement being configured to facilitate the at least one portion of the at least one particular elongated member therethrough, wherein at least one portion of the assembly is positioned inside a container containing a sample fluid; and
affixing at least one portion of the temperature-conducting arrangement within at least one further elongated member which is configured to facilitating the at least one portion of the temperature-conducting arrangement therethrough, wherein a temperature of the particular fluid is substantially the same as a temperature of the sample fluid.

20. The method of claim 19, wherein the assembly includes a sensor which is adapted to measure at least one characteristic of the sample fluid, and wherein the particular fluid is a sensor fluid which is in communication with the sensor.

21. The method of claim 20, wherein the sensor fluid is oil.

22. The method of claim 21, wherein the oil is at least one of a silicone oil, a fluorolube oil, and a propylene glycol oil.

23. The method of claim 19, wherein the at least one particular elongated member is composed of a metallic material.

24. The assembly of claim 1, wherein the temperature-conducting arrangement is composed of a metallic material, and wherein the temperature-conducting arrangement extends for a length which is substantially the same as a length of the at least one further elongated member.

25. The method of claim 19, wherein the step of affixing the at least one portion of the at least one particular elongated member within the temperature-conducting arrangement comprises the step of soldering the at least one particular elongated member to the temperature-conducting arrangement such that at least one portion of a solder forms at least one portion of a side portion of the temperature-conducting arrangement, and wherein the step of affixing the at least one portion of the temperature-conducting arrangement within the at least one further elongated member comprises the step of soldering the temperature-conducting arrangement to the at least one further elongated member.

26. The method of claim 19, further comprising the step of affixing the assembly to the container.

27. The method of claim 19, wherein the assembly comprises a sensor housing arrangement, wherein the at least one particular elongated member is positioned inside the temperature-conducting arrangement, wherein the temperature-conducting arrangement is positioned inside the at least one further elongated member, and wherein the at least one further elongated member is positioned inside the housing arrangement.

28. The method of claim 27, wherein the assembly further comprises a first sensor which is one of coupled to the housing arrangement and positioned inside the housing arrangement, wherein the first sensor is adapted to detect a first fluid pressure of the sample fluid at a first fluid level by acting on the particular fluid.

29. The method of claim 28, wherein the at least one particular elongated member comprises a pair of particular elongated members, wherein a first one of the pair of particular elongated members is adapted to contain the particular fluid, wherein a second one of the pair of particular elongated members is adapted to contain a further fluid, and wherein the step of affixing the temperature-conducting material arrangement to the at least one further elongated member comprises the step of maintaining the temperature of the particular fluid to be substantially the same as a temperature of the further fluid.

30. The method of claim 29, wherein the assembly further comprises a second sensor which is one of coupled to the housing arrangement and positioned inside the housing arrangement, wherein the second sensor is adapted to detect a second fluid pressure of the sample fluid at a second fluid level by acting on the further fluid.

31. The method of claim 30, wherein the assembly further comprises a transmitter situated externally from the container, wherein the transmitter is one of coupled to the housing arrangement and positioned inside the housing arrangement, and wherein the transmitter is adapted to communicate with the first sensor via the particular fluid, and with the second sensor via the further fluid.

32. The method of claim 31, further comprising the step of generating at least one signal corresponding to a density of the sample fluid, wherein at least one of the first sensor and the second sensor is connected to the first end of the at least one further elongated member, and wherein the transmitter is connected to the second end of the at least one further elongated member.

33. The method of claim 32, further comprising the step of determining the density of the sample fluid based on the at least one signal, wherein the assembly further comprises a determining device coupled to the transmitter.

34. The method of claim 26, wherein the container is a tank.

35. The method claim 19, wherein the at least one particular elongated member is a tube, and wherein the at least one further elongated member is a tube.

36. The method of claim 19, wherein the step of affixing the temperature-conducting arrangement to the at least one further elongated member further comprises the step of maintaining a first temperature of the particular fluid provided at a first end of the at least one particular elongated member to be substantially the same as a second temperature of the particular fluid provided at a second end of the at least one particular elongated member.

\* \* \* \* \*